United States Patent
Joyner et al.

(10) Patent No.: US 11,207,519 B2
(45) Date of Patent: Dec. 28, 2021

(54) MODULATING AFFERENT SIGNALS TO TREAT MEDICAL CONDITIONS

(71) Applicant: Mayo Foundation for Medical Education and Research, Rochester, MN (US)

(72) Inventors: Michael j. Joyner, Rochester, MN (US); Bruce D. Johnson, Rochester, MN (US); Thomas P. Olson, Cannon Falls, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 212 days.

(21) Appl. No.: 16/418,307

(22) Filed: May 21, 2019

(65) Prior Publication Data

US 2019/0269923 A1 Sep. 5, 2019

Related U.S. Application Data

(62) Division of application No. 14/383,964, filed as application No. PCT/US2013/029930 on Mar. 8, 2013, now Pat. No. 10,300,281.

(60) Provisional application No. 61/609,169, filed on Mar. 9, 2012.

(51) Int. Cl.
```
A61K 31/4468    (2006.01)
A61N 1/36       (2006.01)
A61N 2/02       (2006.01)
A61K 31/245     (2006.01)
```

(52) U.S. Cl.
CPC ........ *A61N 1/36114* (2013.01); *A61K 31/245* (2013.01); *A61K 31/4468* (2013.01); *A61N 1/3611* (2013.01); *A61N 1/36057* (2013.01); *A61N 1/36117* (2013.01); *A61N 1/36146* (2013.01); *A61N 2/02* (2013.01)

(58) Field of Classification Search
None
See application file for complete search history.

(56) References Cited

U.S. PATENT DOCUMENTS

| | | | |
|---|---|---|---|
| 3,991,770 | A | 11/1976 | LeVeen |
| 5,527,307 | A | 6/1996 | Srisathapat et al. |
| 5,811,463 | A | 9/1998 | Legzdins et al. |
| 6,928,320 | B2 | 8/2005 | King |
| 7,226,442 | B2 | 6/2007 | Sheppard, Jr. et al. |
| 7,232,435 | B2 | 6/2007 | Hildebrand et al. |
| 7,648,677 | B2 | 1/2010 | Santini, Jr. et al. |
| 7,783,362 | B2 | 8/2010 | Whitehurst et al. |
| 8,010,204 | B2 | 8/2011 | Knudson et al. |
| 8,012,119 | B2 | 9/2011 | Estes et al. |
| 9,393,384 | B1 | 7/2016 | Kapur |
| 9,820,798 | B2 | 11/2017 | Schwartz |
| 2003/0216792 | A1 | 11/2003 | Levin et al. |
| 2004/0172085 | A1 | 9/2004 | Knudson et al. |
| 2005/0131485 | A1 | 6/2005 | Knudson et al. |
| 2006/0041277 | A1 | 2/2006 | Deem et al. |
| 2006/0287678 | A1 | 12/2006 | Shafer |
| 2007/0073354 | A1 | 3/2007 | Knudson et al. |
| 2007/0196510 | A1 | 8/2007 | Gerber et al. |
| 2007/0275035 | A1 | 11/2007 | Herman et al. |
| 2008/0213331 | A1 | 9/2008 | Gelfand et al. |
| 2008/0275514 | A1 | 11/2008 | Ben-David |
| 2009/0221549 | A1 | 9/2009 | Gerber |
| 2010/0114244 | A1 | 5/2010 | Manda et al. |
| 2010/0191311 | A1 | 7/2010 | Scheiner et al. |
| 2010/0204741 | A1 | 8/2010 | Tweden |
| 2010/0249859 | A1 | 9/2010 | DiLorenzo |
| 2011/0207758 | A1 | 8/2011 | Sobotka et al. |
| 2012/0016448 | A1 | 1/2012 | Lee |
| 2013/0237948 | A1 | 9/2013 | Donders et al. |
| 2013/0287698 | A1 | 10/2013 | Seward |
| 2014/0024959 | A1 | 1/2014 | Sobotka et al. |
| 2014/0074076 | A1 | 3/2014 | Gertner |
| 2014/0135661 | A1 | 5/2014 | Garrison |
| 2015/0057313 | A1 | 2/2015 | Joyner et al. |
| 2015/0080926 | A1 | 3/2015 | Emery |
| 2015/0133850 | A1 | 5/2015 | Tunev et al. |
| 2015/0305974 | A1 | 10/2015 | Ehrenreich |
| 2017/0065327 | A1 | 3/2017 | Joyner et al. |
| 2017/0112564 | A1 | 4/2017 | Joyner et al. |

FOREIGN PATENT DOCUMENTS

| | | |
|---|---|---|
| EP | 1904160 | 12/2011 |
| WO | WO2000074753 | 12/2000 |
| WO | WO2006022790 | 3/2006 |
| WO | WO2011156439 | 12/2011 |
| WO | WO2015153767 | 10/2015 |
| WO | WO2015153775 | 10/2015 |

OTHER PUBLICATIONS

Kitzman et al., "Exercise Intolerance", Cardiology Clinic, Aug. 2011, vol. 29(3), pp. 461-477. (Year: 2011).*
Torralva et al., "Fentanyl but not Morphine Interacts with Nonopioid Recombinant Human Neurotransmitter Receptors and Transporters", Journal of Pharmacology and Experimental Therapeutics, Sep. 2020, vol. 374, pp. 376-391. (Year: 2020).*
Amann et al., "Implications of group III IV muscle afferents for high-intensity endurance exercise performance in humans," J Physiol., 589(21):5299-5309, Oct. 28, 2011.

(Continued)

*Primary Examiner* — Savitha M Rao
*Assistant Examiner* — Gregg Polansky
(74) *Attorney, Agent, or Firm* — Fish & Richardson P.C.

(57) ABSTRACT

This document provides methods and materials for modulating afferent nerve signals to treat medical conditions such as CHF, CHF respiration, dyspnea, peripheral vascular disease (e.g., peripheral arterial disease or venous insufficiency), hypertension (e.g., age-associated hypertension, resistant hypertension, or chronic refractory hypertension), COPD, sleep apnea, and chronic forms of lung disease where muscle dysfunction is a part of the disease pathophysiology. For example, methods and materials involved in using electrical and/or chemical techniques to block or reduce afferent nerve signals (e.g., nerve signals of group III and/or IV afferents coming from skeletal muscle and/or the kidneys) are provided.

4 Claims, 9 Drawing Sheets

(56) References Cited

OTHER PUBLICATIONS

American Heart Association, "Classes of heart failure," Sep. 30, 2015. Retrieved from the Internet: <URL: http://www.heart.org/HEARTORG/Conditions/HeartFailure/AboutHeartFailure/Classes-of-Heart-Failure_UCM_306328_Article.jsp#>, 2 pages.
Barnes et al, "Aging enhances autonomic support of blood pressure in women," Hypertension, 63(2):303-308. Epub Dec. 9, 2013.
Brinkmann et al., "Catheter-based renal nerve ablation and centrally generated sympathetic activity in difficult-to-control hypertensive patients: prospective case series," Hypertension, 60(6):1485-1490, Epub Oct. 8, 2012.
Daly et al., "Fifty years of open heart surgery at the Mayo Clinic," Mayo Clin Proc., 80(5):636-640, May 2005.
DiBona and Esler, "Translational medicine: the antihypertensive effect of renal denervation," Am J Physiol Regul Integr Comp Physiol., 298(2):R245-R253, Epub Dec. 2, 2009.
Diedrich et al., "The sympathetic nervous system in hypertension: assessment by blood pressure variability and ganglionic blockade," J Hypertension., 21:1677-1686, 2003.
Ditting et al., "Do distinct populations of dorsal root ganglion neurons account for the sensory peptidergic innervation of the kidney?" Am J Physiol Renal Physiol., 297(5):F1427-34. Epub Aug. 19, 2009.
Doyle, "Sir Horace Smirk: Pioneer in drug treatment of hypertension," Hypertension, 17(2):247-250, Feb. 1991.
European Office Action in European Application No. 13757567.6, dated Sep. 19, 2017, 6 pages.
European Search Report for Application No. 13757567.6 dated Dec. 4, 2015, 6 pages.
European Search Report for Application No. 13757567.6 dated Mar. 24, 2016, 11 pages.
Friedman et al., "Influence of lower body positive pressure on upper airway cross-sectional area in drug-resistant hypertension," Hypertension., 61(1):240-245, Epub Nov. 12, 2012.
Hering et al., "Sustained sympathetic and blood pressure reduction 1 year after renal denervation in patients with resistant hypertension," Hypertension, 64(1):118-124, Epub Apr. 14, 2014.
International Preliminary Report on Patentability for PCT/US2015/023890, dated Oct. 13, 2016, 6 pages.
International Preliminary Report on Patentability for PCT/US2015/023900, dated Oct. 13, 2016, 7 pages.
International Preliminary Report on Patentability for PCT/US203/029930 dated Sep. 18, 2014, 13 pages.
International Search Report and Written Opinion for PCT/US2013/029930 dated May 23, 2013, 8 pages.
International Search Report and Written Opinion for PCT/US2015/23890 dated Jul. 2, 2015, 13 pages.
International Search Report and Written Opinion for PCT/US2015/23900 dated Jul. 2, 2015, 15 pages.
Jones, "Altered autonomic support of arterial blood pressure with age in healthy men," Circulation, 104(20):2424-2429, Nov. 13, 2001.
Joyner, "Can physiology zap therapeutic sweet spots in hypertension?" Hypertension, 60(6): 1385-1386, Epub Oct. 8, 2012.
Joyner, "Congestive heart failure: more bad news from exercising muscle?" Circulation, 110(19):2978-2979, Nov. 9, 2004.
Joyner, "Too much is not enough: hypertension and sympathetic vasoconstriction in contracting muscles," Hypertension, 48(4):560-561, Epub Sep. 11, 2006.
Joyner, "Why physiology matters in medicine," Physiology, 26:72-75, 2011.
Neale, "Medtronic's Renal Denervation System Fails," MedPage Today [online] Jan. 9, 2014 [retrieved on Jul. 8, 2015], Retrieved from the Internet: <URL: http://www.medpagetoday.com/Cardiology/Hypertension/43715>, 6 pages.
Olson et al., "Effects of respiratory muscle work on blood flow distribution during exercise in heart failure," J Physiol., 588(Pt 13):2487-2501, Epub May 10, 2010.
Olson et al., "Exercise-disordered breathing in chronic heart failure," Exerc Sport Sci Rev., 34(4):194-201, Oct. 2006.
Olson et al., "Influence of locomotor muscle metaboreceptor stimulation on the ventilatory response to exercise in heart failure," Circ Heart Fail., 3(2):212-219, Epub Jan. 8, 2010.
Schmitt, "Sex differences in alpha-adrenergic support of blood pressure," Clin Auton Res., 20(4):271-275, Epub Mar. 11, 2010.
Schultz et al., "Cardiovascular effects of spinal cord stimulation in hypertensive patients," Pain Physician, 14(1):1-14, Jan.-Feb. 2011.
Wilkins et al., "Autonomic cardiovascular control during a novel pharmacologic alternative to ganglionic blockade," Clin Pharmacol Ther., 83(5):692-701, Epub Aug. 8, 2007.
Woods, "Causes of breathing inefficiency during exercise in heart failure," J Card Fail., 16(10):835-842, Epub Jun. 16, 2010.
Final Office Action in U.S. Appl. No. 15/120,303 dated Nov. 15, 2018, 15 pages.
Non-final Office Action in U.S. Appl. No. 15/120,303 dated May 17, 2018, 24 pages.
Non-final Office Action in U.S. Appl. No. 15/120,315 dated Aug. 30, 2018, 11 pages.
Non-final Office Action in U.S. Appl. No. 15/120,315 dated Feb. 20, 2018, 43 pages.
Reply to Non-final Office Action in U.S. Appl. No. 15/120,303 dated Aug. 14, 2018, 7 pages.
Reply to Office Action in U.S. Appl. No. 15/120,315 dated Jun. 20, 2018, 7 pages.

\* cited by examiner

MODULATING AFFERENT SIGNALS TO TREAT MEDICAL CONDITIONS

CROSS-REFERENCE TO RELATED APPLICATIONS

This application is a divisional of U.S. application Ser. No. 14/383,964, filed Sep. 9, 2014, which is a National Stage application under 35 U.S.C. § 371 of International Application No. PCT/US2013/029930, having an International Filing Date of Mar. 8, 2013, which claims the benefit of U.S. Provisional Ser. No. 61/609,169 filed Mar. 9, 2012. This disclosures of the prior applications are considered part of (and are incorporated by reference in) the disclosure of this application.

STATEMENT AS TO FEDERALLY SPONSORED RESEARCH

This invention was made with government support under HL071478/RR024151/HL046493 awarded by the National Institute of Health. The government has certain rights in the invention.

BACKGROUND

1. Technical Field

This document relates to methods and materials involved in modulating afferent nerve signals to treat medical conditions such as heart failure, congestive heart failure (CHF), heart failure disordered breathing, dyspnea, peripheral vascular disease, hypertension, chronic obstructive pulmonary disease (COPD), and sleep apnea. For example, this document relates to methods and materials involved in using electrical and/or chemical techniques to block or reduce afferent nerve signals.

2. Background Information

Medical conditions such as heart failure, hypertension, and peripheral vascular disease are major public health concerns. For example, nearly 6 million Americans currently live with heart failure and approximately 670,000 to 700,000 new diagnoses are made each year in the U.S. With new diagnostic technologies, improved survival after myocardial infarction, and the increasing age of the population, it is anticipated that this upward trend will continue. This includes both classical systolic heart failure as well the growing population of diastolic heart failure or heart failure with preserved ejection fraction (HFpEF). Data from the National Health and Nutrition Examination Survey, collected from 1988 through 1991, suggested that 24% of the U.S. adult population had hypertension with numbers that may be approaching 30% today. The term "peripheral vascular disease" includes peripheral arterial disease as well as venous insufficiency. It is estimated that 5% of individuals over the age of 50 years have peripheral arterial disease, although the incidence of undiagnosed peripheral arterial disease may be as high as 30%. Venous insufficiency, a form of peripheral vascular disease, has an incidence of about 2 to 5% in the U.S. population. Trends in obesity, diabetes, and inactivity are likely to increase the incidence of these major chronic illnesses.

SUMMARY

This document provides methods and materials for modulating afferent nerve signals to treat medical conditions such as heart failure, CHF, heart failure disordered breathing, dyspnea, peripheral vascular disease (e.g., peripheral arterial disease or venous insufficiency), hypertension (e.g., age-associated hypertension, resistant hypertension, or chronic refractory hypertension), COPD, sleep apnea, and other chronic forms of lung disease where muscle dysfunction is a part of the disease pathophysiology. For example, this document provides methods and materials involved in using electrical and/or chemical techniques to block or reduce afferent nerve signals (e.g., nerve signals of group III and/or IV afferents coming from skeletal muscle and/or the kidneys).

As described herein, blocking or reducing afferent neural feedback (e.g., afferent nerve signals from muscles and/or the kidneys) can reduce symptoms, disrupt pathophysiology, and improve health status in patients suffering from various medical conditions. Any appropriate chemical technique, electrical technique, or combination thereof can be used to reduce or block afferent nerve signals in a manner that results in a clinical improvement for a patient suffering from a medical condition such as heart failure, CHF, heart failure disordered breathing, dyspnea, peripheral vascular disease (e.g., peripheral arterial disease or venous insufficiency), hypertension (e.g., age-associated hypertension, resistant hypertension, or chronic refractory hypertension), COPD, sleep apnea, and chronic forms of lung disease where muscle dysfunction is a part of the disease pathophysiology. For example, an implantable electrode device designed to deliver electrical pulses capable of reducing or blocking nerve signals can be positioned within a mammal (e.g., a human) with heart failure or CHF and suffering from excessive and/or irregular breathing patterns such that the electrode device can reduce or block afferent nerve signals from, for example, muscles and/or the kidneys. While not being limited to any particular mode of action, breathing abnormalities in heart failure or CHF can be driven by sensory nerves in the exercising muscles (see, e.g., FIG. 1). These nerves normally sense the build-up of metabolites (e.g., lactic acid) in the muscle and increase breathing, blood pressure, and heart rate in an effort to improve oxygen delivery in the contracting muscles. In heart failure or CHF, however, they may become overly sensitive and respond prematurely and excessively to these stimuli such that breathing and sympathetic activity rise disproportionately to the actual stimuli. As described herein, reducing or blocking sensory signals that drive ventilation (or the other responses described herein) can increase exercise tolerance, improve quality of life, and blunt a number of pathophysiological cycles that contribute to poor outcomes and death in heart failure or CHF. In addition to sensory nerves in, for example, the leg, excessive stimulation of similar sensory nerves in the kidney likely contribute to the excessive sympathetic activity observed in heart failure (e.g., CHF) and hypertension. Reducing or blocking of these sensory nerves in the kidney can be used as described herein to reduce the marked sympathetic activation seen in resistant hypertension and heart failure (e.g., CHF), thereby having a dramatic effect on the course of these diseases and patient outcomes.

In general, one aspect of this document features a method for increasing exercise tolerance of a mammal having heart failure. The method comprises, or consists essentially of, (a) identifying a mammal having heart failure and reduced exercise tolerance, and (b) applying an electrical therapy signal to a muscle or kidney afferent nerve of the mammal under conditions wherein afferent nerve signals of the muscle or kidney afferent nerve are reduced or blocked. The mammal can be a human. The method can comprise implanting an electrode device within the mammal. The electrical therapy signal can comprise a frequency between about 1 and about 100 Hz, a current intensity between about 1 and about 10 µA, and a pulse width of about 1 to about 10 milliseconds. The method can comprise applying the electrical therapy signal to a muscle afferent nerve. The mammal can be a human, and the method can comprise applying the electrical therapy signal to the muscle afferent nerve in a region within 5 mm of a spinal nerve, ganglion, or epidural space. The mammal can be a human, and the method can comprise applying the electrical therapy signal to the muscle afferent nerve in a region within 3 mm of a spinal nerve or ganglion. The method can comprise applying the electrical therapy signal to a kidney afferent nerve. The mammal can be a human, and the method can comprise applying the electrical therapy signal to the kidney afferent nerve in a region within 5 mm of a kidney afferent nerve. The mammal can be a human, and the method can comprise applying the electrical therapy signal to the kidney afferent nerve in a region within 3 mm of a kidney afferent nerve. The electrical therapy signal can be delivered by an electrode connected to an implanted neurostimulator control unit. The electrical therapy signal can be an intermittent stimulus that cycles continuously.

In another aspect, this document features a method for increasing exercise tolerance of a mammal having heart failure. The method comprises, or consists essentially of, (a) identifying a mammal having heart failure and reduced exercise tolerance, and (b) applying a composition comprising a nerve blocking agent to a muscle or kidney afferent nerve of the mammal under conditions wherein afferent nerve signals of the muscle or kidney afferent nerve are reduced or blocked. The mammal can be a human. The method can comprise applying the composition to a muscle afferent nerve. The mammal can be a human, and the method can comprise applying the composition to the muscle afferent nerve in a region within 5 mm of a spinal nerve, ganglion, or epidural space. The mammal can be a human, and the method can comprise applying the composition to the muscle afferent nerve in a region within 3 mm of a spinal nerve, ganglion, or epidural space. The method can comprise applying the composition to a kidney afferent nerve. The mammal can be a human, and wherein the method can comprise applying the composition to the kidney afferent nerve in a region within 5 mm of a kidney afferent nerve. The mammal can be a human, and the method can comprise applying the composition to the kidney afferent nerve in a region within 3 mm of a kidney afferent nerve. The nerve blocking agent can be selected from the group consisting of clonidine, morphine, fentanyl, midazolam, lidocaine, and baclofen.

In another aspect, this document features a method for treating a medical condition of a mammal. The method comprises, or consists essentially of, (a) identifying a mammal having the medical condition, and (b) applying an electrical therapy signal to a muscle or kidney afferent nerve of the mammal under conditions wherein afferent nerve signals of the muscle or kidney afferent nerve are reduced or blocked. The mammal can be a human. The method can comprise implanting an electrode device within the mammal. The electrical therapy signal can comprise a frequency between about 1 and about 100 Hz, a current intensity between about 1 and about 10 µA, and a pulse width of about 1 to about 10 milliseconds. The method can comprise applying the electrical therapy signal to a muscle afferent nerve. The mammal can be a human, and the method can comprise applying the electrical therapy signal to the muscle afferent nerve in a region within 5 mm of a spinal nerve, ganglion, or epidural space. The mammal can be a human, and the method can comprise applying the electrical therapy signal to the muscle afferent nerve in a region within 3 mm of a spinal nerve, ganglion, or epidural space. The method can comprise applying the electrical therapy signal to a kidney afferent nerve. The mammal can be a human, and the method can comprise applying the electrical therapy signal to the kidney afferent nerve in a region within 5 mm of a kidney afferent nerve. The mammal can be a human, and the method can comprise applying the electrical therapy signal to the kidney afferent nerve in a region within 3 mm of a kidney afferent nerve. The electrical therapy signal can be delivered by an electrode connected to an implanted neurostimulator control unit. The electrical therapy signal can be an intermittent stimulus that cycles continuously. The medical condition can be selected from the group consisting of heart failure, heart failure disordered breathing, dyspnea, peripheral vascular disease, hypertension, chronic obstructive pulmonary disease, and sleep apnea.

In another aspect, this document features a method for treating a medical condition of a mammal. The method comprises, or consists essentially of, (a) identifying a mammal having the medical condition, and (b) applying a composition comprising a nerve blocking agent to a muscle or kidney afferent nerve of the mammal under conditions wherein afferent nerve signals of the muscle or kidney afferent nerve are reduced or blocked. The mammal can be a human. The method can comprise applying the composition to a muscle afferent nerve. The mammal can be a human, and the method can comprise applying the composition to the muscle afferent nerve in a region within 5 mm of a spinal nerve, ganglion, or epidural space. The mammal can be a human, and the method can comprise applying the composition to the muscle afferent nerve in a region within 3 mm of a spinal nerve, ganglion, or epidural space. The method can comprise applying the composition to a kidney afferent nerve. The mammal can be a human, and the method can comprise applying the composition to the kidney afferent nerve in a region within 5 mm of a kidney afferent nerve. The mammal can be a human, and the method can comprise applying the composition to the kidney afferent nerve in a region within 3 mm of a kidney afferent nerve. The nerve blocking agent can be selected from the group consisting of clonidine, morphine, fentanyl, midazolam, lidocaine, and baclofen. The medical condition can be selected from the group consisting of heart failure, congestive heart failure, heart failure disordered breathing, dyspnea, peripheral vascular disease, hypertension, chronic obstructive pulmonary disease, and sleep apnea.

In another aspect, this document features a method for reducing blood pressure within a mammal. The method comprises, or consists essentially of, (a) identifying a mammal having elevated blood pressure, and (b) applying an electrical therapy signal to a muscle or kidney afferent nerve of the mammal under conditions wherein afferent nerve signals of the muscle or kidney afferent nerve are reduced or blocked. The mammal can be a human. The method can comprise implanting an electrode device within the mammal. The electrical therapy signal can comprise a frequency between about 1 and about 100 Hz, a current intensity between about 1 and about 10 µA, and a pulse width of about 1 to about 10 milliseconds. The method can comprise applying the electrical therapy signal to a muscle afferent nerve. The mammal can be a human, and the method can comprise applying the electrical therapy signal to the muscle afferent nerve in a region within 5 mm of a spinal nerve, ganglion, or epidural space. The mammal can be a human, and the method can comprise applying the electrical therapy signal to the muscle afferent nerve in a region within 3 mm of a spinal nerve, ganglion, or epidural space. The method can comprise applying the electrical therapy signal to a kidney afferent nerve. The mammal can be a human, and the method can comprise applying the electrical therapy signal to the kidney afferent nerve in a region within 5 mm of a kidney afferent nerve. The mammal can be a human, and the method can comprise applying the electrical therapy signal to the kidney afferent nerve in a region within 3 mm of a kidney afferent nerve. The electrical therapy signal can be delivered by an electrode connected to an implanted neurostimulator control unit. The electrical therapy signal can be an intermittent stimulus that cycles continuously.

In another aspect, this document features a method for reducing blood pressure within a mammal. The method comprises, or consists essentially of, (a) identifying a mammal having elevated blood pressure, and (b) applying a composition comprising a nerve blocking agent to a muscle or kidney afferent nerve of the mammal under conditions wherein afferent nerve signals of the muscle or kidney afferent nerve are reduced or blocked. The mammal can be a human. The method can comprise applying the composition to a muscle afferent nerve. The mammal can be a human, and the method can comprise applying the composition to the muscle afferent nerve in a region within 5 mm of a spinal nerve, ganglion, or epidural space. The mammal can be a human, and the method can comprise applying the composition to the muscle afferent nerve in a region within 3 mm of a spinal nerve, ganglion, or epidural space. The method can comprise applying the composition to a kidney afferent nerve. The mammal can be a human, and the method can comprise applying the composition to the kidney afferent nerve in a region within 5 mm of a kidney afferent nerve. The mammal can be a human, and the method can comprise applying the composition to the kidney afferent nerve in a region within 3 mm of a kidney afferent nerve. The nerve blocking agent can be selected from the group consisting of clonidine, morphine, fentanyl, midazolam, lidocaine, and baclofen.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
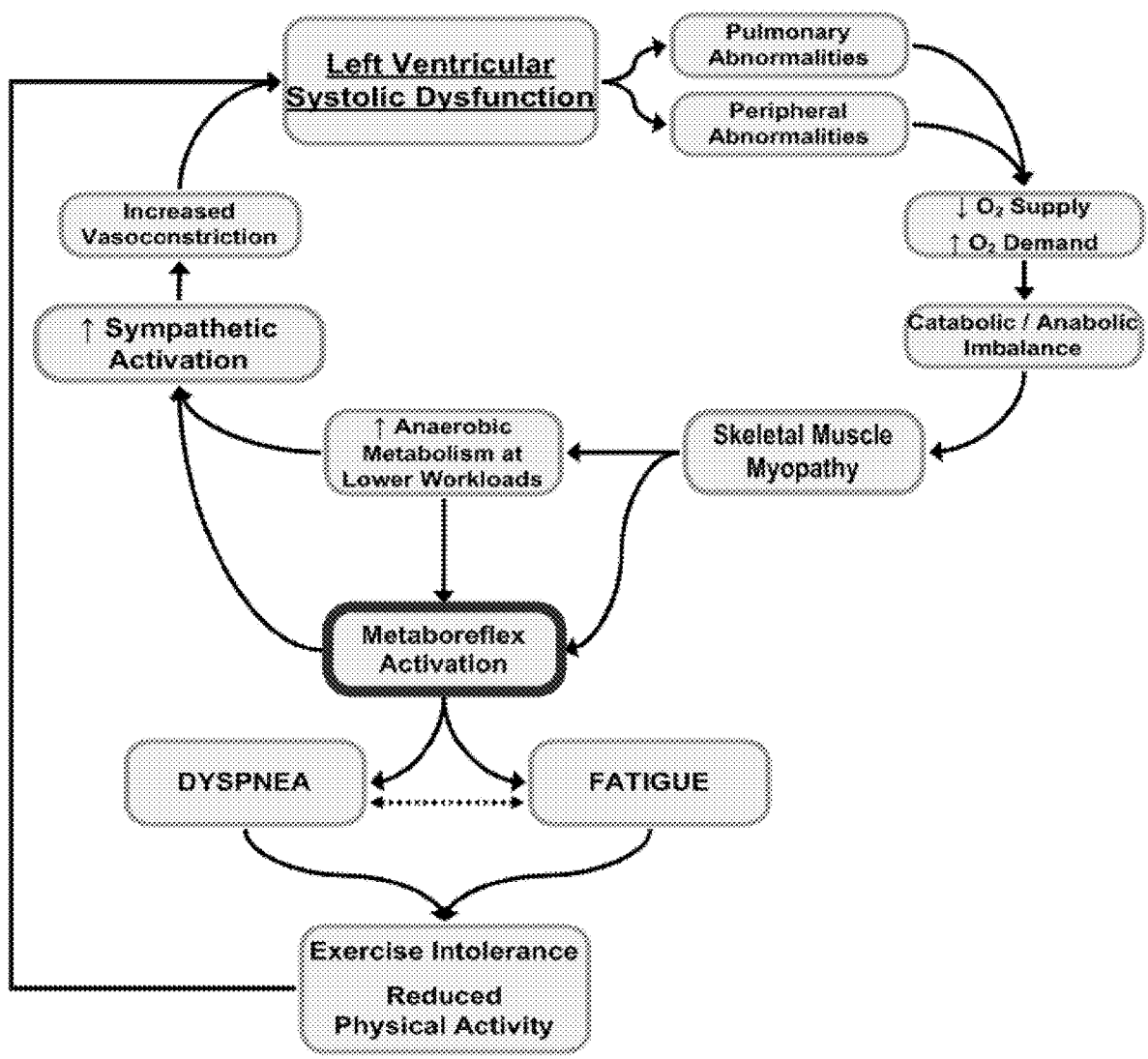
FIG. 1 is a diagram of an overview of the influence of locomotor muscle neural feedback on sympathetic nervous system activation and continued progression of heart failure.

This document provides methods and materials for modulating afferent nerve signals to treat medical conditions such as heart failure, CHF, heart failure disordered breathing, dyspnea, peripheral vascular disease (e.g., peripheral arterial disease or venous insufficiency), hypertension (e.g., age-associated hypertension, resistant hypertension, or chronic refractory hypertension), COPD, sleep apnea, and chronic forms of lung disease where muscle dysfunction is a part of the disease pathophysiology. For example, this document provides methods and materials for using electrical and/or chemical techniques to block or reduce afferent nerve signals (e.g., nerve signals of group III and/or IV afferents coming from skeletal muscle and/or the kidneys).

As described herein, reducing or blocking nerve signals from group III and/or IV afferents coming from muscle (e.g., skeletal muscle), one or both kidneys, and/or both can result in improved quality of life, reduced disordered breathing, and improved exercise tolerance for patients suffering from CHF, can result in reduced blood pressure for patients with elevated blood pressure, can result in improved exercise tolerance for patients with peripheral vascular disease, and/or can result in improved exercise tolerance for patients suffering from sleep apnea. In some cases, electrical and/or chemical techniques can be used to reduce or block afferent nerve signals by targeting one or more of the locations set forth in Table 1. For example, a medical condition described herein can be treated by reducing or blocking afferent nerve signals by targeting the afferents at locations near the spinal column such as near lumbar 2-5 (e.g., L2, L3, L4, or L5), sacral 1-2 (e.g., S1 or S2), cervical 2-5 (e.g., C2, C3, C4, or C5), and/or thoracic 4-12 (e.g., T4, T5, T6, T7, T8, T9, T10, T11 or T12)). In some cases, a medical condition described herein can be treated by reducing or blocking afferent nerve signals by targeting the afferents and/or ganglia such as a celiac plexus, a hepatic plexus, a splenic plexus, a gastric plexus, a pancreatic plexus, a suprarenal plexus, a renal plexus, a testicular plexus, an ovarian plexus, a superior mesenteric plexus, and/or an inferior mesenteric plexus.

TABLE 1

Targeted locations of afferent nerves for treating medical conditions.

| Medical Condition | Afferent Nerves or ganglia | Particular Locations |
|---|---|---|
| Heart failure | Spinal Afferents | T4 through S2<br>Thoracic levels to block renal afferents<br>Lumbar and sacral to block muscle afferents |
| | Celiac Plexus<br>Renal Plexus<br>Suprarenal Plexus | To reduce sympathoexcitatory afferent signals from the kidney and viscera |
| | Dorsal Root Ganglia (e.g., target multiple numbers, e.g. 4-5, on both sides of the spine) | L1-5 |
| Heart failure respiration | Spinal Afferents | T4 through S2<br>Thoracic levels to block renal afferents<br>Lumbar and sacral to block muscle afferents |
| | Dorsal Root Ganglia (e.g., target multiple numbers, e.g. 4-5, on both sides of the spine) | L1-5 |
| dyspnea | Spinal Afferents | T4 through S2<br>Thoracic levels to block renal afferents<br>Lumbar and sacral to block muscle afferents |
| | Dorsal Root Ganglia (e.g., target multiple numbers, e.g. 4-5, on both sides of the spine)<br>phrenic afferents | L1-5 |
| peripheral vascular disease | Spinal afferents | T4 through S2<br>Thoracic levels to block renal afferents<br>Lumbar and sacral to block muscle afferents |
| hypertension | Spinal afferents | T4 through S2<br>Thoracic levels to block renal afferents<br>Lumbar and sacral to block muscle afferents |
| | Cleiac Plexus<br>Renal Plexus<br>Suprarenal plexus<br>Superior mesenteric plexus<br>Inferior mesenteric plexus | To reduce sympathoexcitatory afferent signals from the kidney and viscera |
| | Dorsal root ganglia (e.g., target multiple numbers, e.g. 4-5, on both sides of the spine) | T6-12 |
| COPD | Spinal afferents | T4 through S2<br>Thoracic levels to block renal afferents<br>Lumbar & Sacral to block muscle afferents |
| | Dorsal root ganglia (e.g., target multiple numbers, e.g. 4-5, on both sides of the spine) | T6-12 |
| sleep apnea | Spinal afferents | T4 through S2<br>Thoracic levels to block renal afferents<br>Lumbar and sacral to block muscle afferents |
| | Cleiac Plexus<br>Renal Plexus<br>Suprarenal plexus<br>Superior mesenteric plexus<br>Inferior mesenteric plexus | Thoracic levels to block renal afferents<br>Lumbar & Sacral to block muscle afferents<br>To reduce sympathoexcitatory afferent signals from the kidney and viscera |
| | Dorsal root ganglia (e.g., target multiple numbers, e.g. 4-5, on both sides of the spine) | T6-12 |

Any appropriate electrical and/or chemical technique can be used to reduce or block afferent nerve signals. For example, one or more electrode devices, one or more drug pump devices, or a combination one or more electrode devices and one or more drug pump devices can be used to reduce or block afferent nerve signals. In some cases, a mild cooling device, a vibration device, or an ultrasound device can be used to block afferent nerve signals (e.g., to block afferent nerve signals transiently). In some cases, an implantable electrode device can be used to deliver electrical therapy signals to afferent nerves in a manner that reduces or blocks afferent nerve signals. Examples of electrode devices that can be used to deliver electrical therapy signals to afferent nerves in a manner that reduces or blocks afferent nerve signals include, without limitation, those devices configured to include one or more electrodes as described elsewhere (see, e.g., U.S. Pat. Nos. 8,010,204, 7,783,362, 6,928,320, PCT Publication No. WO/2011/156439, U.S. Patent Application Publication No. 20040172085, U.S. Patent Application Publication No. 20050131485, U.S. Patent Application Publication No. 20070073354, U.S. Patent Application Publication No. 20100191311, U.S. Patent Application Publication No. 20120016448, U.S. Patent Application Publication No. 20100114244, or EP1904160). In some cases, neurostimulator devices such as a Medtronic™ Soletra or Kinetra can be implanted into a mammal and configured to deliver electrical therapy signals to afferent nerves in a manner that reduces or blocks afferent nerve signals. For example, a lead (or electrode) of a neurostimulator device can be positioned within 7.5 mm (e.g., within 7, 6, 5, 4, 3, 2, or 1 mm) of a nerve or ganglion of interest within a patient suffering from heart failure (e.g., CHF) to provide electrical therapy signals to afferent nerves. In some cases, a battery powered neurostimulator control unit of a neurostimulator device can be implanted (e.g., in the patient's chest) and can have one or more extensions connecting the neurostimulator control unit to one or more electrodes positioned at a targeted afferent nerve location (e.g., a targeted afferent nerve location set forth in Table 1). In some cases, one or more electrodes can be positioned unilaterally or bilaterally within a mammal to be treated (e.g., human to be treated).

Any appropriate electrical therapy signals can be used provided that they reduce or block afferent nerve signals. For example, electrical therapy signals designed to reduce or block afferent nerve signals can have a frequency of between about 1 Hz and about 100 Hz, can have a current intensity between about 1 µA and about 10 µA, and a pulse width of about 1 milliseconds to about 10 milliseconds. In some cases, electrical therapy signals can be intermittent with pauses ranging for about 10 seconds to about 120 seconds. In some cases, electrical therapy signals can be discontinuous with rest periods of up to about 12 hours. For some exercise applications, electrical therapy signals can be used only during exercise or periods of increased physical activity.

In some cases, appropriate electrical therapy signals can have a frequency of about 5 Hz and a current intensity of about 3 µA. In some cases, electrical therapy signals can be a series of applied electrical current (e.g., a train). In some cases, electrical therapy signals include a train with inter-train rest periods. For example, electrical parameters can include rest periods in which no current is applied. In some cases, the rest period can be from about 5 seconds to about 120 seconds.

In some cases, electrical therapy signals can be used to reduce or block afferent nerve signals continuously (e.g., 24 hours a day) or for certain periods of a day. For example, electrical therapy signals can be used to reduce or block afferent nerve signals from renal sources during the night and electrical therapy signals can be used to reduce or block afferent nerve signals at dorsal root ganglia during the day. In some cases, a patient having peripheral vascular disease can be treated as described herein by reducing or blocking afferent nerve signals continuously (e.g., 24 hours a day). In some cases, a patient with hypertension can be treated as described herein by reducing or blocking afferent nerve signals from renal sources at night and when the patient is lying down. In some cases, a patient in need of improved ventilation (e.g., a CHF patient) or a patient with hypertension can be treated by implanting one or more electrode devices having the ability to sense activity. In such cases, the device(s) can deliver reducing or blocking electrical therapy signals during periods of increased activity levels.

In some cases, more than one location within a mammal's body can be target to reduce or block afferent nerve signals. For example, one or more electrode devices can be implanted into a mammal such that renal afferent nerve signals are reduced or blocked during the night and muscular afferent nerve signals (e.g., afferent nerve signals at dorsal root ganglia) are reduced or blocked during the day or during periods of activity.

Figure 8:
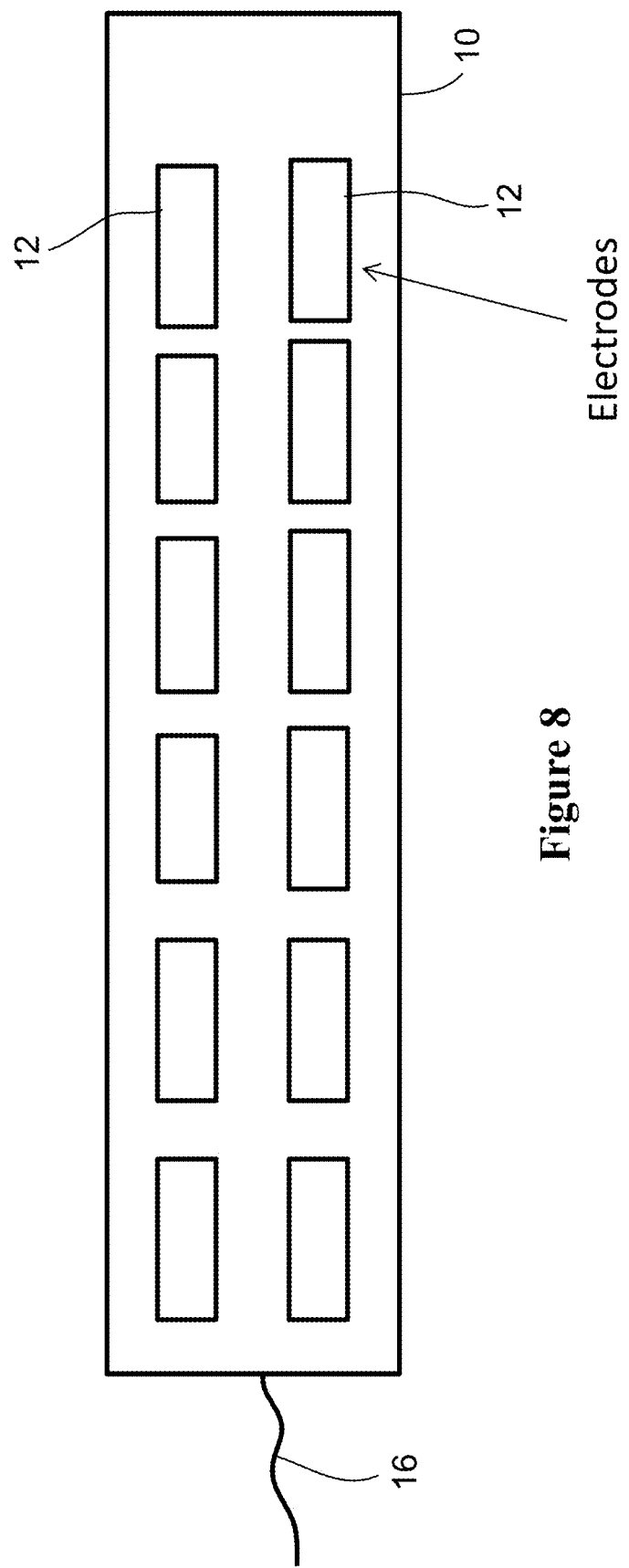
FIG. 8 is a top view of an electrode lead having multiple independently controlled electrodes.
Figure 9:
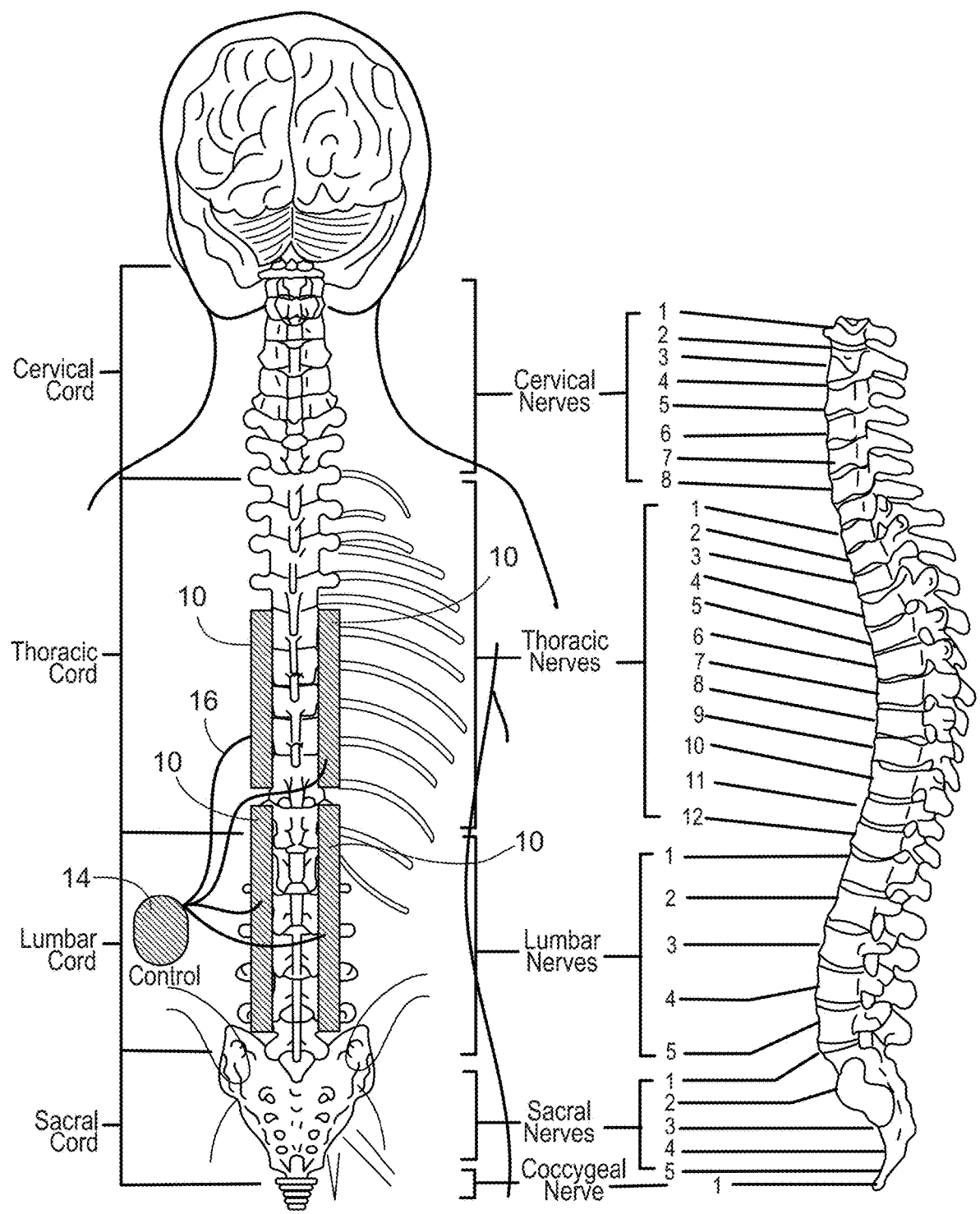
FIG. 9 is a schematic of the human spine and nervous system with two electrode leads place on each side of the spine.

In some cases, both leg (e.g., muscular afferents) and renal afferents can be blocked with the same device (e.g., using different leads, or a lead with a wide span with multiple electrodes; see e.g., FIGS. 8 and 9). In some cases, both afferent groups can be blocked continuously, or the leg afferents can be blocked during the day and the renal afferents can be blocked at night. In some cases, the pattern of nerve blocking can be synchronized to CPAP (continuous positive airway pressure).

As shown in FIG. 9, electrode leads can be implanted to block multiple afferents groups at the same time and on either or both sides of the spine. In some cases, afferent groups can be blocked at different anatomic locations at the same time (e.g., the T6-12 leads and the L1-5 leads both blocking at the same time) or at different time periods (e.g., T6-12 leads at night, and the L1-5 leads during the day). As shown in FIG. 8, an electrode lead can include multiple independently controlled electrodes designed to allow a user to select which electrodes are activated to block various afferent groups. The activation can occur at different time periods (day/night) or cycle at different time points to prevent accommodation.

In some cases, an implantable drug pump device can be used to deliver one or more nerve blocking agents to afferent nerves in a manner that reduces or blocks afferent nerve signals. Examples of nerve blocking agents that can be used to reduce or block afferent nerve signals as described herein include, without limitation, clonidine, morphine, fentanyl, midazolam, lidocaine, baclofen, other local anesthetics, and substance P antagonists. Any appropriate drug pump device can be used to deliver one or more nerve blocking agents to a location described herein to reduce or block afferent nerve signals. Examples of such drug pump devices that can be configured to deliver one or more nerve blocking agents to a location described herein included, without limitation, those drug pump devices described in U.S. Pat. Nos. 7,226,442; 7,648,677; 8,012,119; 5,527,307; International Patent Application Publication No. WO2000/074753, or U.S. Patent Application Publication No. 2007/0275035.

Any appropriate dose of a nerve blocking agent can be delivered as described herein provided that that amount reduces or blocks afferent nerve signals. For example, when delivering fentanyl, between about 5 µg and about 25 µg of fentanyl can be delivered per hour. When delivering clonidine, between about 10 µg and about 100 µg of clonidine can be delivered per hour. When delivering baclofen, between about 0.1 µg and about 10 µg of baclofen can be delivered per hour.

The invention will be further described in the following examples, which do not limit the scope of the invention described in the claims.

EXAMPLES

Example 1—Locomotor Muscle Afferents Contribute to Ventilatory Control During Exercise in Heart Failure Patients Reduced ventilatory efficiency is a hallmark of heart failure and is linked to disease severity and a poor prognosis. The following was performed to determine if neurologic feedback from locomotor muscles is a mechanism responsible for altered ventilatory efficiency and to determine the impact of reducing or blocking locomotor muscle afferent feedback on ventilation ($V_E$) during exercise in heart failure patients.

Briefly, five heart failure patients with reduced systolic function (age=60±11 years, height=1.81±0.03 m, weight=94±7 kg, ejection fraction=27±5%, NYHA I-III class=2±0) underwent two 5-minute submaximal steady-state exercise sessions at 60% peak work (placebo (PLA) vs. regional neural blockade via intrathecal injection of fentanyl (RNB)). Using aseptic technique and local anesthesia, 50 µg of fentanyl was administered via a 22 g Whitaker needle. Breath-by-breath measures included $V_E$, breathing frequency (fb), tidal volume ($V_T$), end-tidal carbon dioxide ($PETCO_2$), oxygen consumption ($VO_2$), and carbon dioxide production ($VCO_2$). Central chemoreceptor sensitivity also was measured via $CO_2$ rebreathe.

Figure 2:
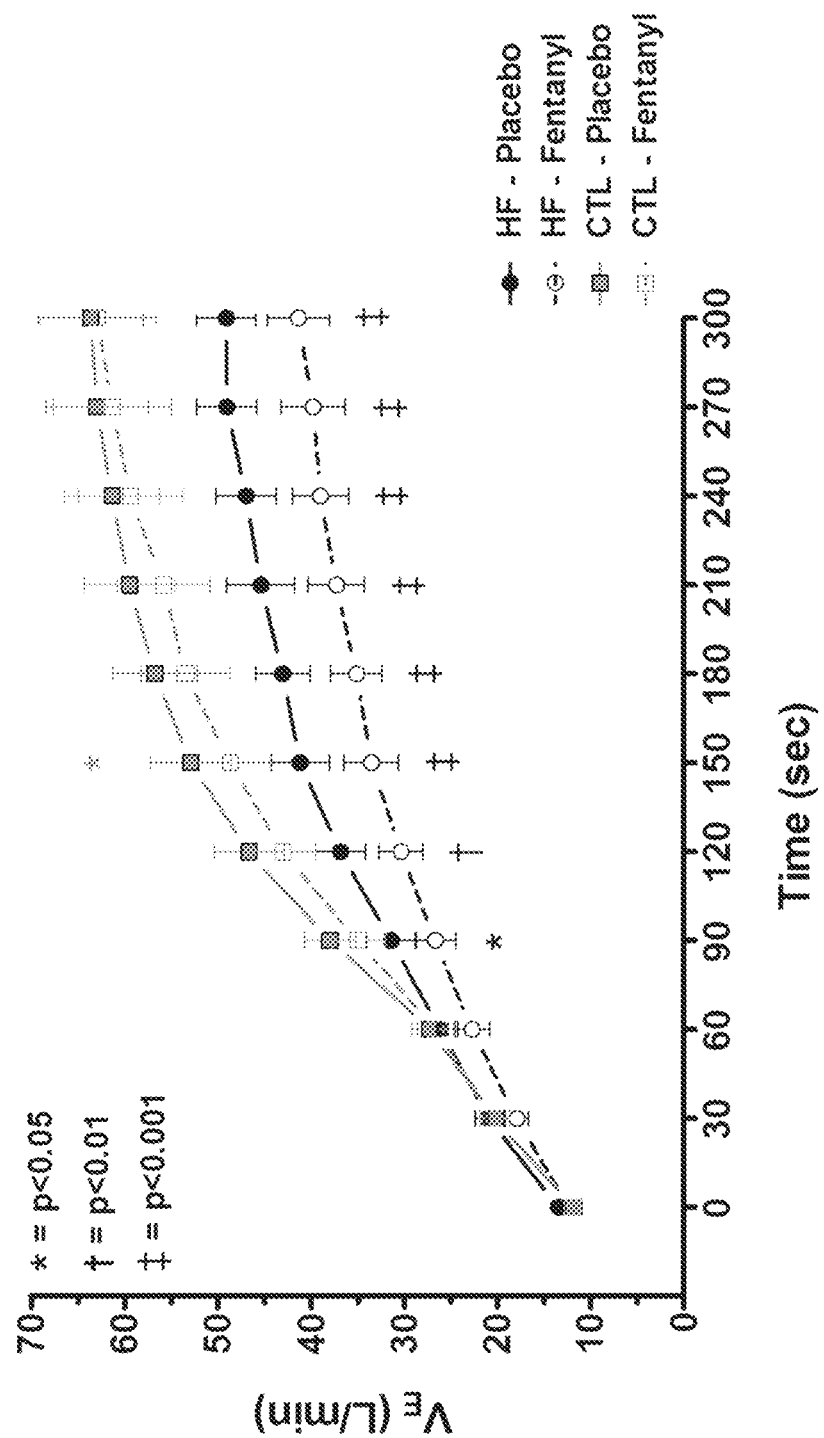
FIG. 2 is a graph plotting minute ventilation, $V_E$ (L/minute), versus time (seconds) for control (CTL) and heart failure (HF) patients treated with placebo or fentanyl.
Figure 3:
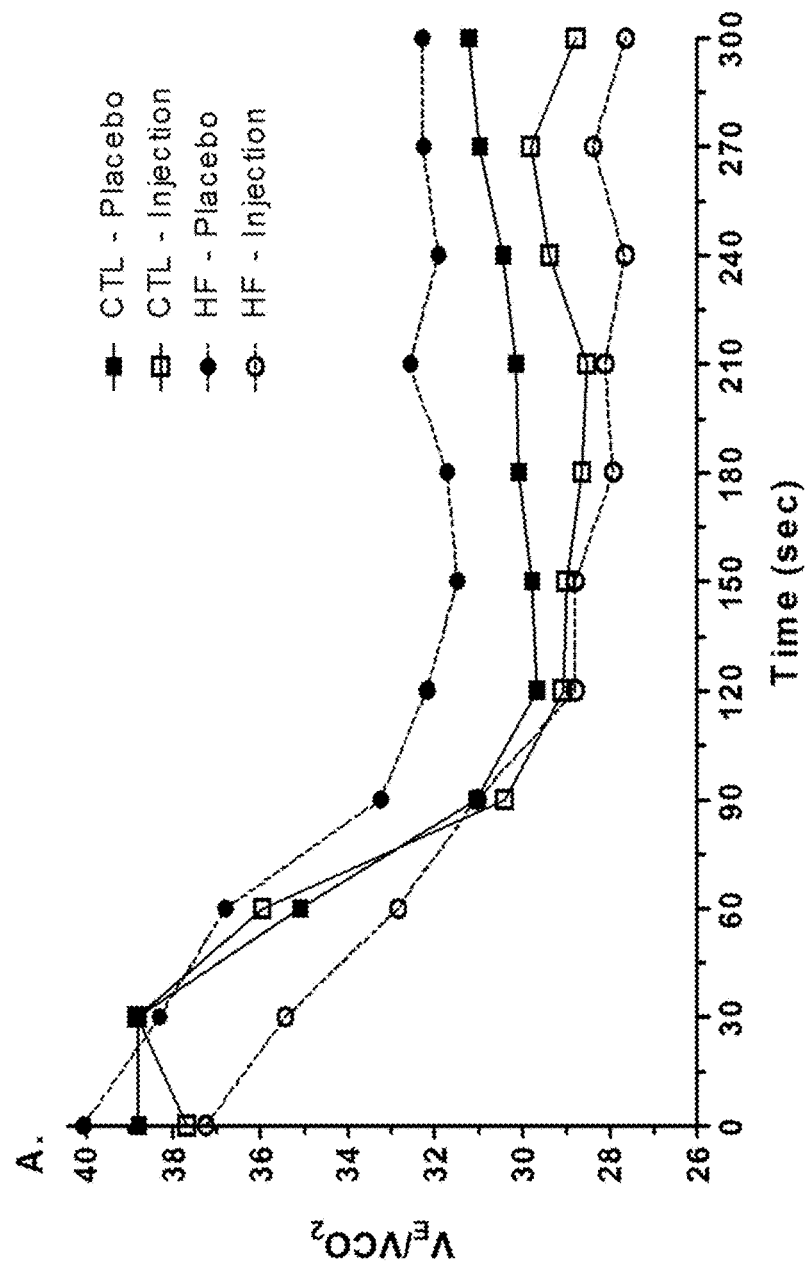
FIG. 3 is a graph plotting ventilatory efficiency, $V_E/VCO_2$, versus time (seconds) for control (CTL) and heart failure (HF) patients treated with placebo or fentanyl.
Figure 4:
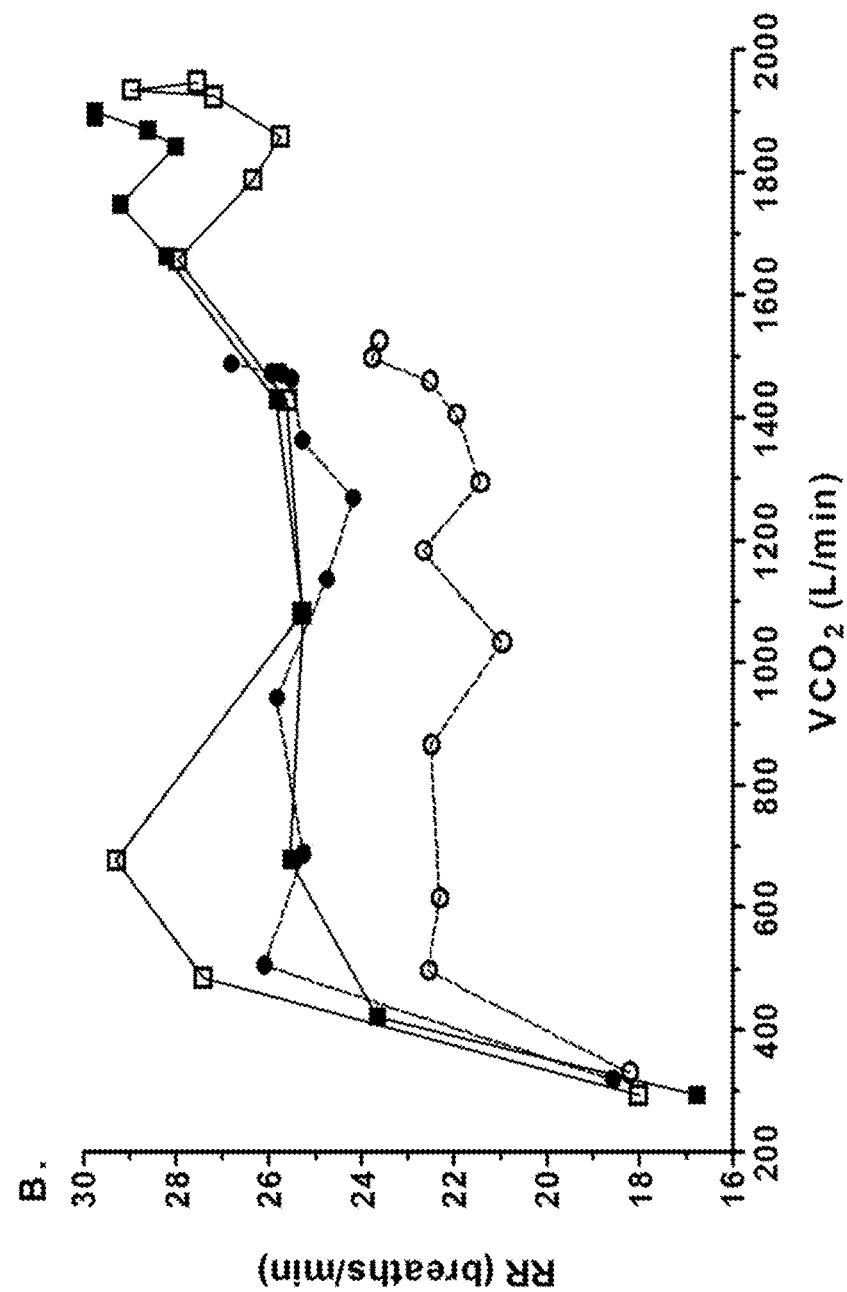
FIG. 4 is a graph plotting respiratory rate, RR (breaths/minute), versus carbon dioxide production, $VCO_2$ (L/minute), for control (CTL) and heart failure (HF) patients treated with placebo or fentanyl. The symbols for this figure are the same as those of FIG. 3.
Figure 5:
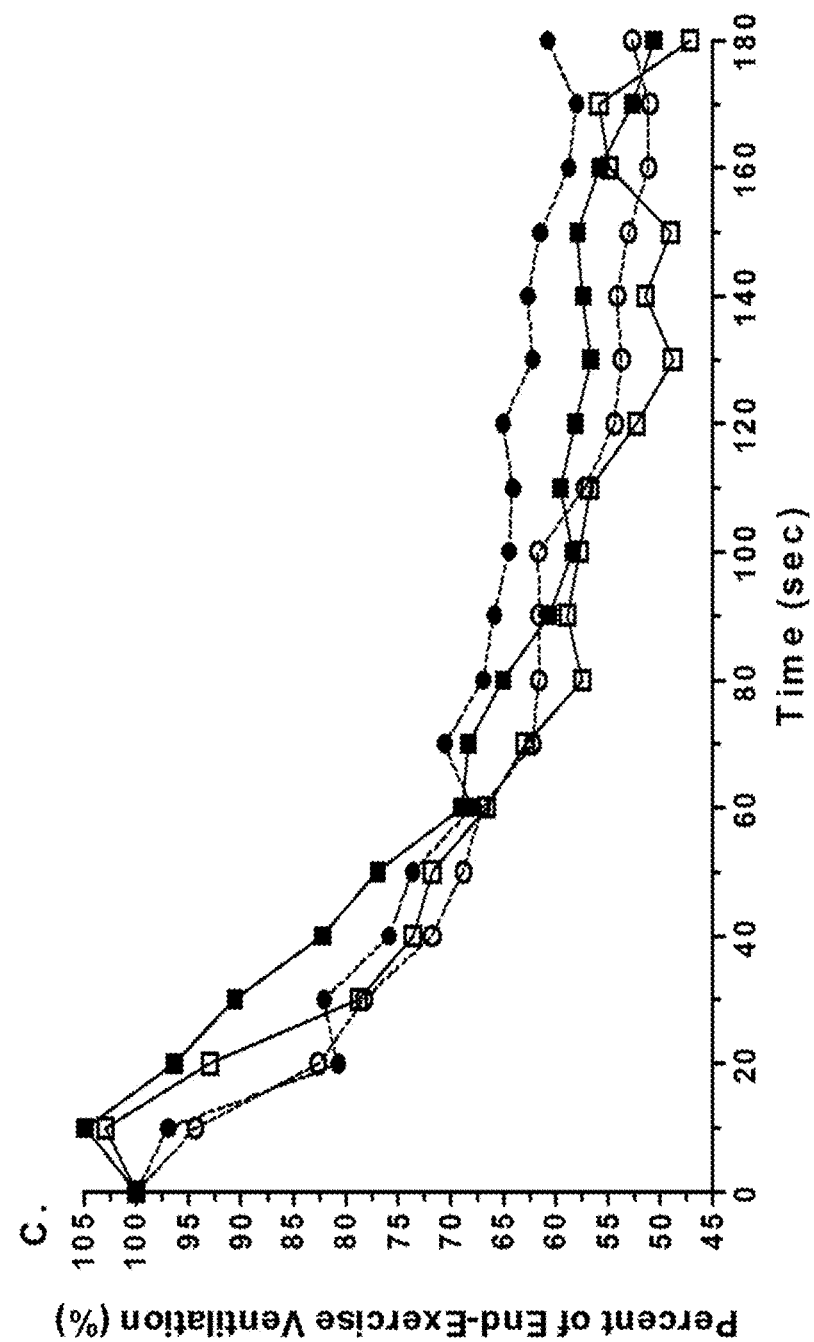
FIG. 5 is a graph plotting the percent of end-exercise ventilation versus $VCO_2$ (L/minute) for control (CTL) and heart failure (HF) patients treated with placebo or fentanyl. The symbols for this figure are the same as those of FIG. 3.
Figure 6:
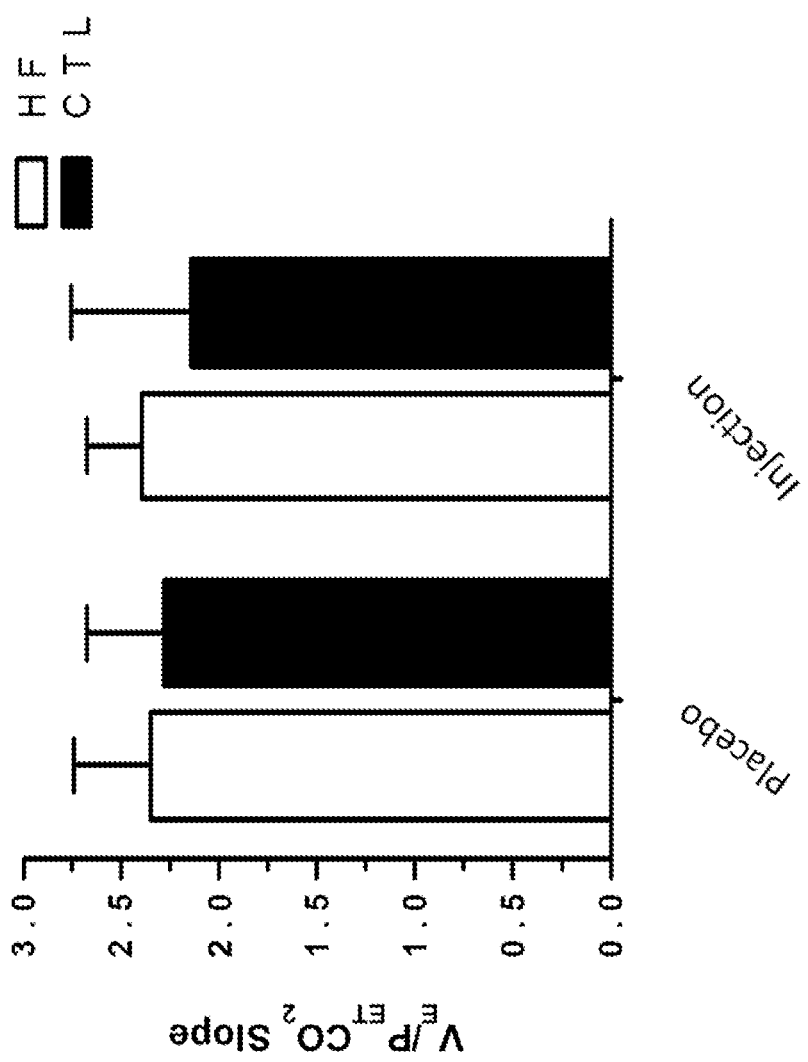
FIG. 6 is a bar graph plotting the influence of intrathecal injection of fentanyl on central chemoreceptor sensitivity.

At end exercise, there was no difference in $VO_2$ (1.4±0.2 vs. 1.4±0.2 L/min, p=0.43). $V_E$ was reduced with RNB (48.0±6.5 vs. 41.8±6.0 L/min, p<0.05) through a reduction in fb (27.2±5.2 vs. 23.9±4.2 breaths/min, p<0.01) with no change in $V_T$ (1.8±0.2 vs. 1.8±0.2 L/min, p=0.81) (FIG. 2). Additionally, the $V_E/VCO_2$ ratio was reduced (improved) with RNB (33.2±3.5 vs. 28.2±2.8, p<0.05). After exercise, there was no difference between the conditions for chemoreceptor sensitivity ($V_E/PETCO_2$ slope=2.4±0.9 vs. 2.4±0.6, p=0.80). See, e.g., FIGS. 3-6.

These results demonstrate that in heart failure patients, blocking afferent neural feedback from the locomotor muscles during exercise reduces $V_E$ and improves ventilatory efficiency.

Figure 7:
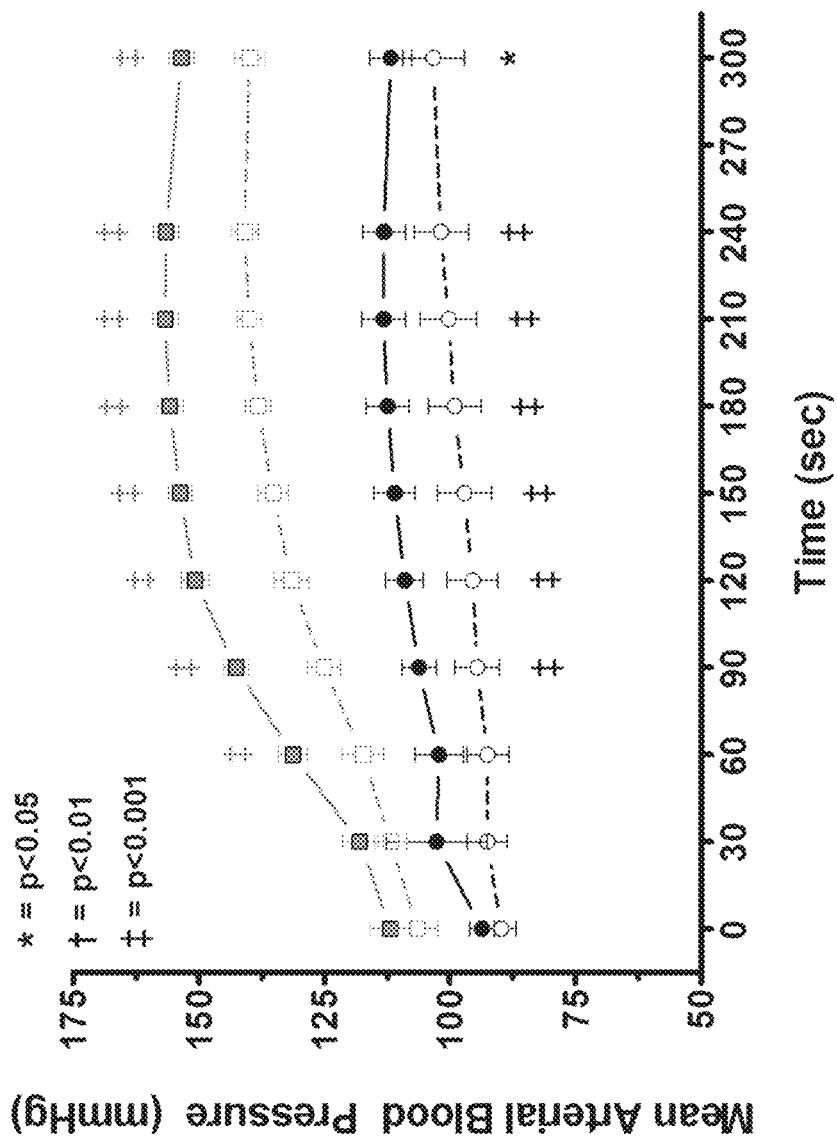
FIG. 7 is a graph plotting mean arterial blood pressure (mmHg) versus time (seconds) for control (CTL) and heart failure (HF) patients treated with placebo or fentanyl. The symbols for this figure are the same as those of FIG. 2.

Mean arterial blood pressure measurements also were obtained from the PLA- and RNB-treated patients. A significant reduction in mean arterial blood pressure was detected for RNB-treated patients (FIG. 7). These results demonstrate that the blood pressure response to exercise can be reduced in selected patient groups.

These results also demonstrate that arterial $CO_2$ can be increased at rest post afferent blockade. This rise in $PaCO_2$ post blockade can occur despite the fact that the $CO_2$ ventilatory response (a test of central chemosensitivity) remains constant as does hand grip strength (a sign that the medication did not migrate centrally). These results also demonstrate that the metaboreceptors can be active even at rest in heart failure and that blocking these fibers can have long term pathophysiological benefits.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing exercise tolerance of a mammal having heart failure, wherein said method comprises:
    (a) identifying a mammal having heart failure and reduced exercise tolerance, and
    (b) applying a composition comprising fentanyl to a muscle afferent nerve of said mammal under conditions wherein afferent nerve signals of said muscle afferent nerve are reduced or blocked.

2. The method of claim 1, wherein said mammal is a human.

3. The method of claim 2, wherein said method comprises applying said composition to said muscle afferent nerve in a region within 5 mm of a spinal nerve, ganglion, or epidural space.

4. The method of claim 2, wherein said method comprises applying said composition to said muscle afferent nerve in a region within 3 mm of a spinal nerve, ganglion, or epidural space.

* * * * *